(12) United States Patent
Mannino et al.

(10) Patent No.: US 8,993,764 B2
(45) Date of Patent: Mar. 31, 2015

(54) USE OF ORIPAVINE AS A STARTING MATERIAL FOR BUPRENORPHINE

(75) Inventors: Anthony Mannino, Maryland Heights, MO (US); Erik R. Hoefgin, Springfield, IL (US); Lloyd P. Hill, St. Louis, MO (US); Henry J. Buehler, St. Louis, MO (US)

(73) Assignee: Mallinckrodt LLC, Hazelwood, MO (US)

( * ) Notice: Subject to any disclaimer, the term of this patent is extended or adjusted under 35 U.S.C. 154(b) by 1162 days.

(21) Appl. No.: 12/159,025

(22) PCT Filed: Dec. 18, 2006

(86) PCT No.: PCT/US2006/048479
§ 371 (c)(1),
(2), (4) Date: Jun. 24, 2008

(87) PCT Pub. No.: WO2007/081506
PCT Pub. Date: Jul. 19, 2007

(65) Prior Publication Data
US 2008/0312441 A1    Dec. 18, 2008

Related U.S. Application Data

(60) Provisional application No. 60/756,380, filed on Jan. 5, 2006.

(51) Int. Cl.
*C07D 489/02* (2006.01)
*C07D 489/12* (2006.01)

(52) U.S. Cl.
CPC ............ *C07D 489/12* (2013.01); *C07D 489/02* (2013.01)
USPC .......................................................... 546/44

(58) Field of Classification Search
CPC ................................................... C07D 489/02
USPC .................................................... 546/44, 74
See application file for complete search history.

(56) References Cited

U.S. PATENT DOCUMENTS

| | | | |
|---|---|---|---|
| 3,285,914 A * | 11/1966 | Gordon .......................... | 544/125 |
| 3,318,886 A | 5/1967 | Brown et al. | |
| 3,415,830 A | 12/1968 | Nagata et al. | |
| 4,275,205 A | 6/1981 | Kotick et al. | |
| 4,347,361 A | 8/1982 | Quick et al. | |
| 4,795,813 A | 1/1989 | Schwartz | |
| 5,849,915 A | 12/1998 | Kim et al. | |
| 6,067,749 A * | 5/2000 | Fist et al. ................... | 47/58.1 R |
| 6,376,221 B1 | 4/2002 | Fist et al. | |
| 6,723,894 B2 * | 4/2004 | Fist et al. ...................... | 800/260 |
| 2004/0077863 A1 | 4/2004 | Scammells et al. | |
| 2004/0106761 A1 | 6/2004 | Zha et al. | |
| 2004/0197428 A1 | 10/2004 | Fist et al. | |

FOREIGN PATENT DOCUMENTS

| | | |
|---|---|---|
| CA | 2023858 A1 * | 2/1991 |
| EP | 1 439 179 | 7/2004 |

OTHER PUBLICATIONS

Greene and Wuts "Protective Groups in Organic Synthesis" 3rd Edition, Wiley, 1999, pp. 22-27, 76-85.*
Ujvary "A Practical Synthesis of 3-n-Propylphenol, a Component of Tsetse Fly Attractant Blends" Organic Process Research & Development 2003, 7, 585-587.*
Werner "Synthesis of Buprenorphine from Oripavine via N-Demethylation of Oripavine Quaternary Salts" J. Org. Chem. 2011, 76, 4628-4634.*
Abel et al., "A novel regiospecific *N* to *O*-methyl transferase activity in the biotransformation of a thebaine derivative with *Cunninghamella echinulata* NRRL 1384", The Royal Society of Chemistry, 2002, p. 1762-1763, XP-002430206.

* cited by examiner

*Primary Examiner* — David K O Dell

(57) ABSTRACT

There is provided a method for the synthesis of norbuprenorphine, and ultimately buprenorphine, utilizing oripavine as the starting material. Conventional methods of producing buprenorphine utilize thebaine as the starting material, requiring an O-demethylation step, typically a low to moderate yield transformation. The present use of oripavine as a starting material does not require an O-demethylation step, since the oripavine molecule lacks an O-3 methyl group.

4 Claims, No Drawings

USE OF ORIPAVINE AS A STARTING MATERIAL FOR BUPRENORPHINE

CROSS REFERENCE TO RELATED APPLICATIONS

This application is a national stage application of PCT/US2006/048479, filed Dec. 18, 2006, which claims the benefit of U.S. Provisional Application No. 60/756,380 filed Jan. 05, 2006.

BACKGROUND OF INVENTION

Buprenorphine acts as a mixed agonist/antagonist and it is an important treatment option for opiate addiction and analgesia.

The conventional synthetic route used world-wide to prepare buprenorphine utilizes thebaine as the starting material.

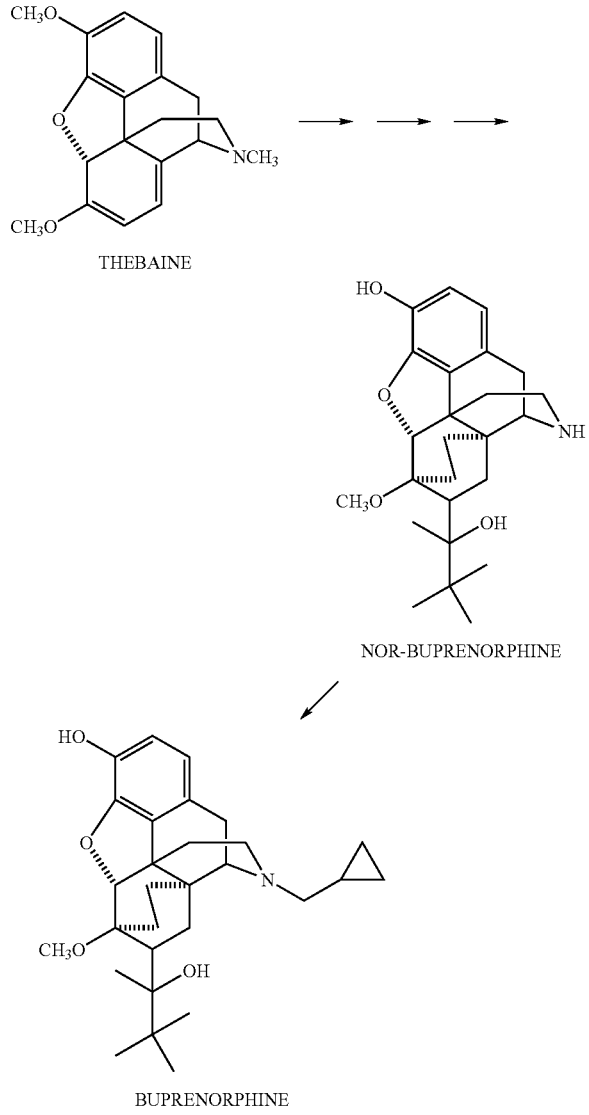

Through a series of chemical reactions, thebaine is converted into nor-buprenorphine, the immediate precursor to buprenorphine. The final step adds a cyclopropyl methyl group to the nitrogen to form buprenorphine from nor-buprenorphine.

An outline of the conventional series of reactions from thebaine to buprenorphine follows:

1. Reaction of thebaine with methyl vinyl ketone to form the 4+2 reaction product.
2. Hydrogenation of the carbon-carbon double bond.
3. Addition of a tertiary butyl group via a Grignard Reaction.
4. An N-demethylation, via a two step reaction sequence.
5. An O-demethylation reaction and an N-cyano hydrolysis.
6. Addition of the cyclopropyl methyl group to form buprenorphine.

A drawback of this conventional production scheme is that the O-demethylation step is considered a low to moderate yield transformation. There is therefore a need for a norbuprenorphine/buprenorphine production scheme that does not include an O-demethylation step.

SUMMARY OF INVENTION

An aspect of the present invention is to provide a method for producing norbuprenorphine utilizing oripavine as the starting material. The method comprises:

reacting oripavine according to Formula I with methyl vinyl ketone to form a compound according to Formula II;

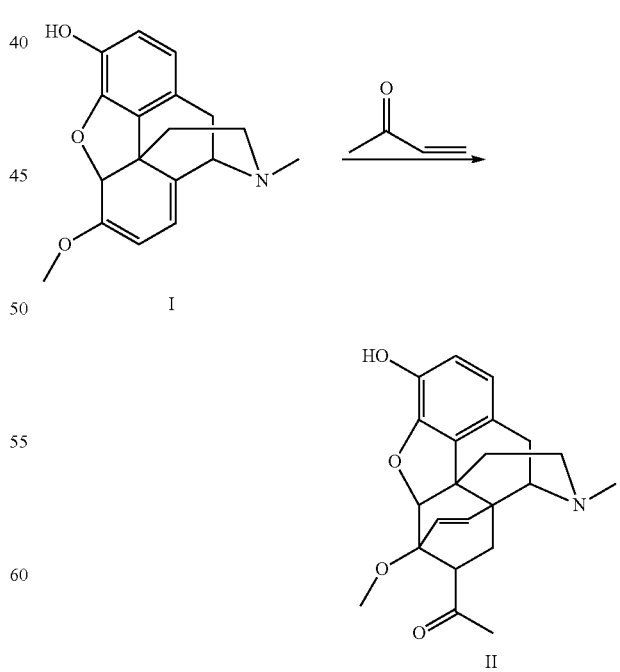

hydrogenating the compound according to Formula II to form a compound according to Formula III;

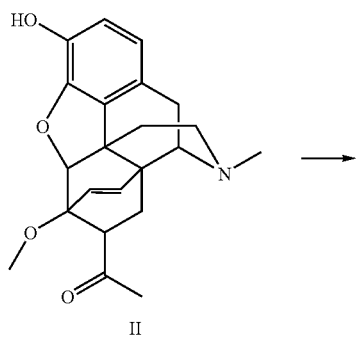

II

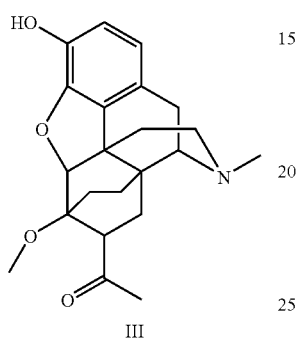

III adding a t-butyl group to the compound according to Formula III to form a compound according to Formula X; and

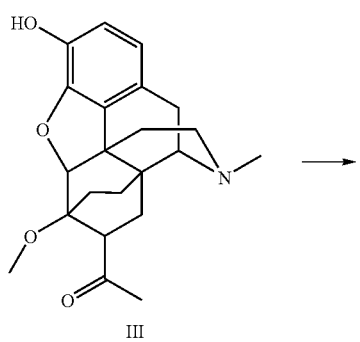

III

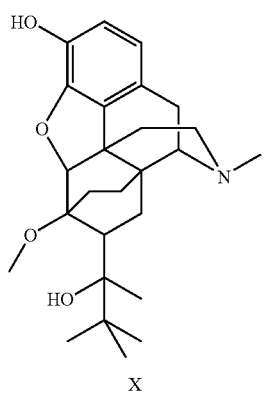

X demethylating the nitrogen of the compound according to Formula X to form norbuprenorphine, Formula VIII.

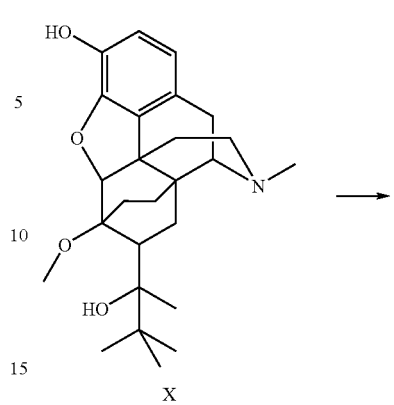

X

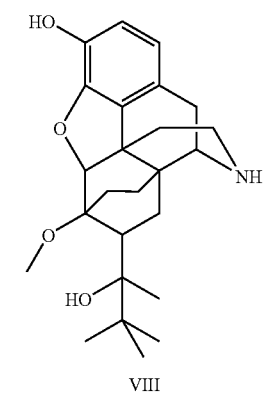

VIII

Another aspect of the present invention is to provide a method of making buprenorphine utilizing oripavine as the starting material.

DETAILED DESCRIPTION

There is provided a method utilizing oripavine as the preferred starting material for the synthesis of nor-buprenorphine and optionally buprenorphine. Oripavine is a naturally occurring alkaloid of *Papaver somniferum*. The key difference between the conventional technology and the present use of oripavine as a starting material is that the O-demethylation step, typically a low to moderate yield transformation, is not needed since the oripavine molecule lacks an O-3 methyl group. In a synthesis involving several steps, it is advantageous to have only high yield reactions in order for the overall transformation to be economical. Since the present oripavine based synthesis does not require the O-3 demethylation step, the overall yield from oripavine provides an improved yield over that traditionally achieved when thebaine is used as the starting material. The conversion route from oripavine to produce buprenorphine is convenient and more straightforward as compared to other synthetic routes.

An illustrative embodiment of the steps for converting oripavine into norbuprenorphine, and optionally buprenorphine, is as follows:

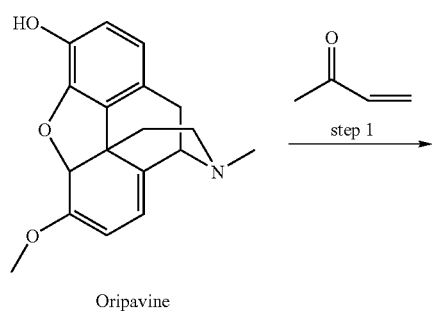
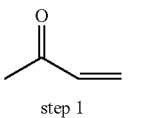
Oripavine
I
step 1
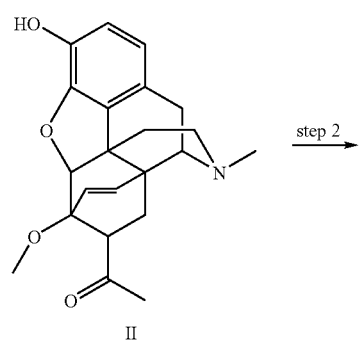
II
step 2
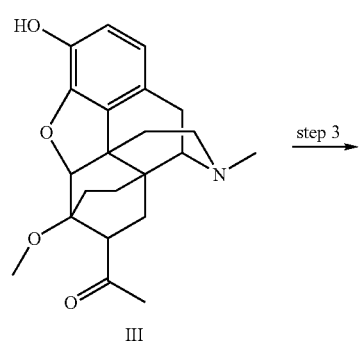
III
step 3
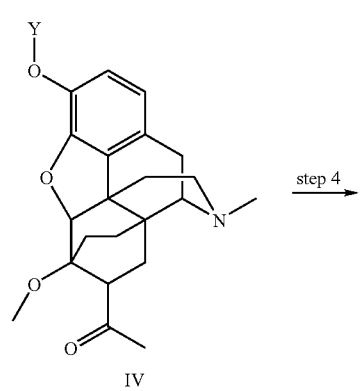
IV
step 4
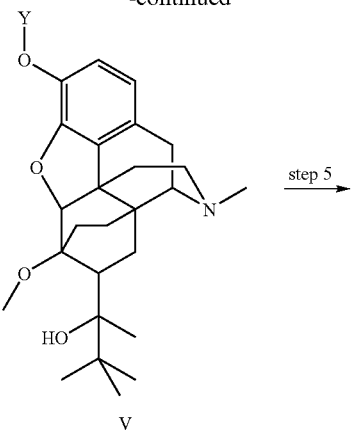
V
step 5
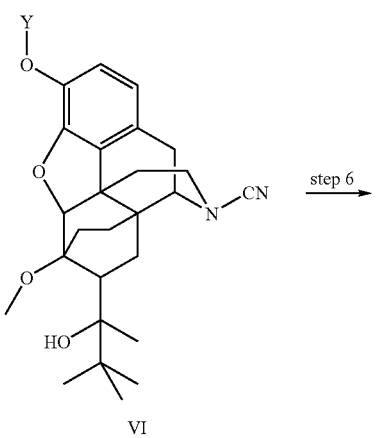
VI
step 6
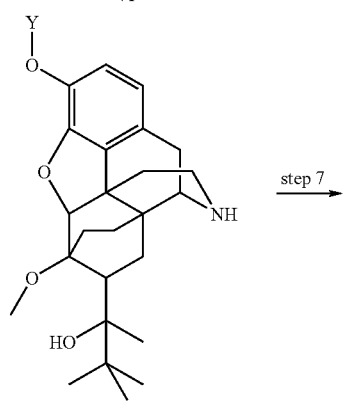
VII
step 7
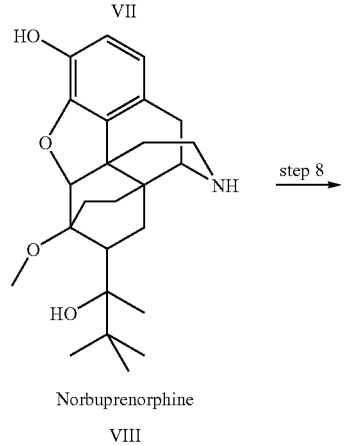
Norbuprenorphine
VIII
step 8

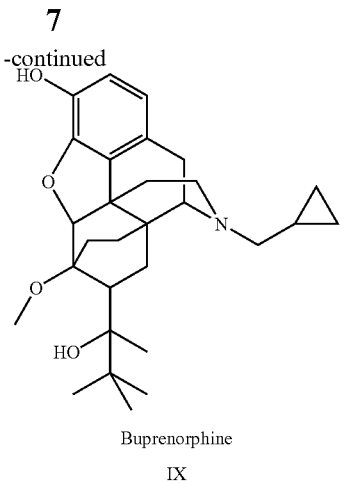

Buprenorphine

IX

The sequence outlined above is an illustrative embodiment presented to show the transformations required, but is not limited as to the order in which the transformations may be employed. In an alternative embodiment, the hydrogenation of the Diels-Alder double bond can also be accomplished as part of step 7 when the removal of the Y protecting group is through catalytic hydrogenation.

Step 1:

The first step involves reaction of the oripavine with methyl vinyl ketone. This addition reaction may be accomplished by any conventional method known in the art. An illustrative embodiment is a Diels-Alder reaction in which the oripavine and methyl vinyl ketone are dissolved in a solvent and refluxed until the reaction is substantially complete. Illustrative suitable solvents include isopropyl alcohol, methanol, ethanol, toluene and mixtures thereof. The reaction mixture is then filtered to isolate the Diels-Alder adduct solids. Typical reactions result in at least about an 85% yield of at least about 98% purity.

Step 2:

The second step involves the hydrogenation of the C—C double bond. In an illustrative embodiment, the Diels-Alder adduct formed in step 1 was charged to a reaction vessel with Pd/Carbon catalyst, then dissolved in a solvent. A presently preferred solvent is methanol, but any suitable solvent may be used, including methanol, ethanol, isopropyl alcohol, acetic acid and mixtures thereof. The hydrogenation takes place under nitrogen at an elevated pressure and temperature. The temperature and pressure are selected to insure substantial completion of the reaction, as is well known in the art. An illustrative temperature range typical of this reaction is about 50-90° C., with about 60° C. being preferred and an illustrative pressure range typical of this reaction is about 20-60 psi, with about 35 psi being preferred. The reaction mixture is filtered to remove the catalyst and the resulting filtrate reduced under vacuum to yield the product according to Formula III.

Step 3:

Optional step 3 discloses the addition of a protecting group Y to form a compound according to Formula IV. The preferred method using oripavine as the starting material for nor-buprenorphine and then buprenorphine utilizes an O-3 protecting group. However, the reaction can be accomplished without the use of the protection group, although the overall yield may be compromised. Further, the protecting group may be removed simultaneously with another step thereby eliminating one chemical step. Addition of an O-3 protecting group may minimize unwanted chemical reactions involving the unprotected phenol function at the 3-position. Illustrative suitable protecting groups include benzyl, O-t-butyl and silyl groups.

In an illustrative embodiment, the reduced Diels-Alder adduct according to Formula III and ground $K_2CO_3$ are added ($K_2CO_3$ not soluble) in chloroform and benzyl bromide, heated and refluxed. After cooling to room temperature, the reaction mixture is filtered to remove the $K_2CO_3$. The filtrate is then reduced under vacuum and azeo dried in toluene.

Step 4:

The fourth step utilizes the crude material according to Formula IV, formed in step 3, in a Grignard reaction. Under moisture free conditions and further under an inert atmosphere, t-BuMgCl is added, followed by anhydrous toluene. The solution is distilled until a pot temperature of about 100° C. is achieved, and the compound according the Formula IV is added. The reaction is quenched, and the temperature of the reaction mixture lowered. The organic and aqueous layers are separated, and the organic layer is concentrated under vacuum yielding an oily residue. The oily residue is then purified resulting in a compound according to Formula V, of up to about 93% purity.

In an alternate embodiment, the t-butyl group is added using a t-butyl lithium reagent, as is well known in the art.

The N-demethylation reaction may be accomplished by any suitable method known in the art. In the illustrative embodiment shown in steps 5 and 6, the methyl group is first converted into a nitrile in step 5, followed by reduction of the nitrile group in step 6.

Step 5:

In an illustrative embodiment of step 5, the tertiary alcohol starting material according to Formula V is dissolved in a solvent, flushed with an inert atmosphere, and then $K_2CO_3$ and cyanogen bromide are added. This reaction mixture is then refluxed until the reaction is substantially complete, cooled to room temperature and filtered to remove the $K_2CO_3$. The reaction mixture is then extracted and the organic layers reduced and dried under vacuum. The resulting solid is purified yielding up to about 93% clean material after drying.

Step 6:

In an illustrative embodiment, potassium hydroxide is dissolved in diethylene glycol and heated. The N—CN compound according to Formula VII is added and the reaction mixture heated until the reaction is substantially complete. After cooling to room temperature, distilled water is added and the resulting solid collected and dried, with up to about 100% yield.

The N-demethylation may be accomplished by any method know to those skilled in the art without departing from the instant method.

Step 7:

The seventh step involves the removal of the optional protecting group. In the illustrative embodiment, the Y protecting group added in step 3 is removed. In this embodiment, the secondary amine starting material may be catalytically removed by Pd/Carbon in a suitable solvent. Suitable solvents include methanol, ethanol, isopropyl acetate and mixtures thereof. The resulting filtrate is dried under vacuum to yield norbuprenorphine. In another embodiment, the Y protecting group may be removed with an acid, such as HCl, HOAc, HF or an F anion.

Step 8:

Finally the norbuprenorphine is optionally converted to buprenorphine as illustrated in step 8. In an illustrative embodiment, the norbuprenorphine is converted to buprenorphine.

In an illustrative embodiment, a mixture of norbuprenorphine, a mild base, and cyclopropylmethyl bromide are heated in an oilbath at about 80-100° C. until the reaction is substantially complete. The reaction mixture is then added over 5 minutes to 160 ml of water, with mechanical stirring, yielding a gum. The mixture is stirred and filtered, and the filter cake is washed with water. The HPLC will show about 90% by area of desired product, and 0.2-0.5% of an N-butenyl substituted impurity. The resulting product is dried, and then boiled in alcohol, cooled, and filtered to yield buprenorphine.

In the alternative, norbuprenorphine can be converted to buprenorphine by reductive amination, or by acylation followed by reduction of the amide.

In an alternative embodiment, the hydrogenation step 2 is performed on the crude reaction mixture formed in step 1, thereby providing a one-pot reaction scheme for forming a compound according to Formula III.

The oripavine, methyl vinyl ketone and isopropyl alcohol are heated under pressure. Upon cooling, a Pd—C catalyst is added, and the reaction mixture is heated under pressure until the reaction is substantially complete. The product is then solubilized and the catalyst removed by filtration. The filtrate is then concentrated under vacuum.

In another alternative embodiment, illustrated below, a method for producing norbuprenorphine, and optionally buprenorphine, from oripavine, without the use of a protecting group on O-3. The individual reactions are as discussed in more detail above.

The method comprises:

a) reacting the oripavine according to Formula I with methyl vinyl ketone to form a compound according to Formula II;

b) hydrogenating the compound according to Formula II to form a compound according to Formula III;

c) adding a t-butyl group to the compound according to Formula III to form a compound according to Formula X; and

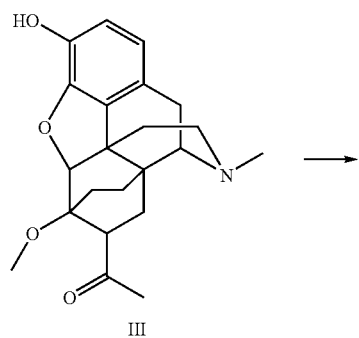

III

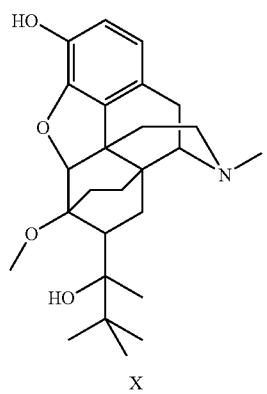

X d) demethylating the nitrogen compound according to Formula X to form norbuprenorphine, Formula VIII.

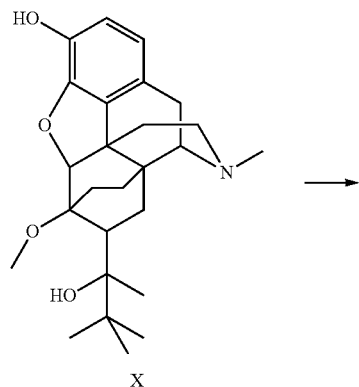

X

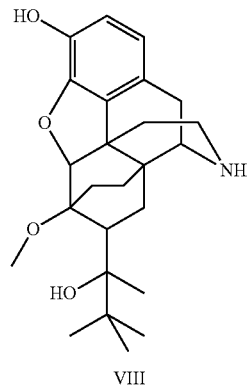

VIII

EXAMPLES

Example 1

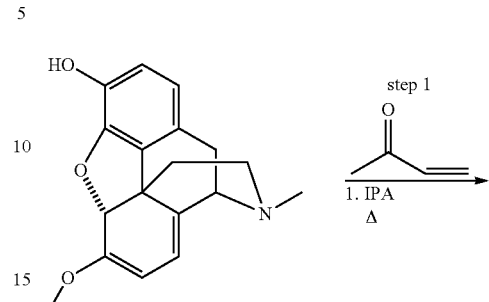

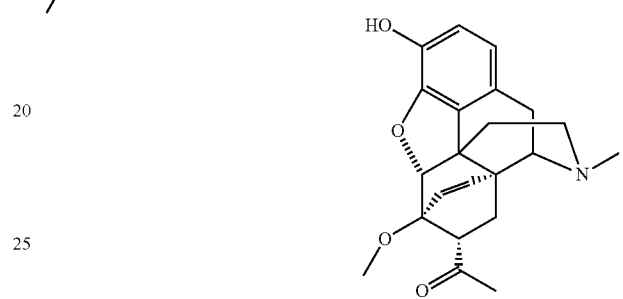

The oripavine (150 g, 505 mmol) was charged to a 1-L 3-neck jacketed flask equipped with a mechanical stirring device, a thermocouple, and a reflux condenser. The reactants were dissolved in 750 mL of isopropyl alcohol (IPA), equivalent to 5 mL/g. 90% technical grade methyl vinyl ketone (MVK) was added in two portions. Each portion consisted of 68.0 mL (747 mmol, 1.5 equivalents), with the second addition occurring approximately 8 hours after the first. After the first addition of MVK, the reaction mixture was heated to reflux at about 78° C., and the temperature was slowly increased to near 84° C. as the MVK was consumed. The reaction was allowed to continue overnight after the second addition of MVK, and was stopped in the morning by slowly cooling to 5-10° C. After stirring for approximately 2 hours at 5-10° C., the reaction mixture was filtered to isolate the solids, washing with cold IPA. After drying, an 85% yield of adduct with a purity of 98-99% by area after correcting for the assay of the starting material was recovered.

Example 2

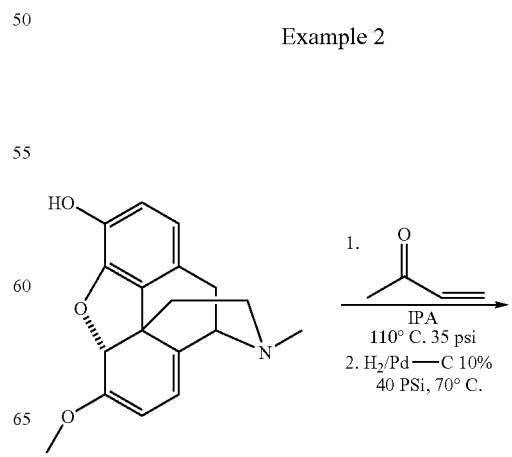

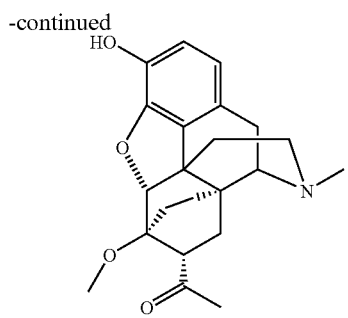

a) A pressure vessel was charged with 9 g (77% assay) of oripavine, 5.6 ml of methyl vinyl ketone and 45 ml of isopropyl alcohol. The vessel was sealed and the contents were heated to 110° C. resulting in a pressure of 35 psi. After 4 hours the reaction mixture was cooled to room temperature and 0.6 g of Pd—C (10%) was added. The mixture was hydrogenated at 70° C. and 40 psi for 24 hours. The product was solubilized using methanol, and the catalyst was removed by filtering through a plug of hyflo. The filtrate was concentrated in vacuo to afford 8.6 g.

Example 3

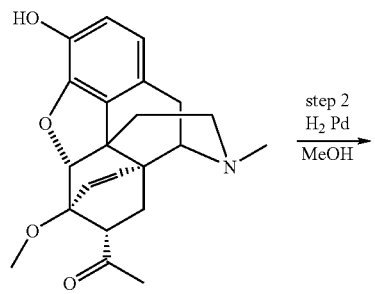

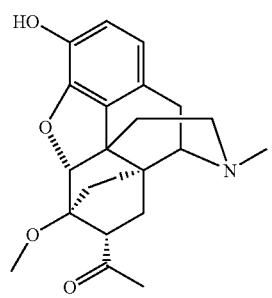

The Diels-Alder adduct (13 g, 35 mmol) formed in Example 1 was charged to a reaction vessel with a 5% charge (dry basis) of 10% Pd/Carbon catalyst (1.3 g). The adduct was then dissolved/suspended in 10 ml/g of methanol (130 mL). After flushing the vessel eight times with 40 psi $N_2$, and four times with 40 psi $H_2$, the pressure was returned to 40 psi $H_2$. The temperature was elevated to 60° C. where the hydrogenation was carried out over approximately eight hours in a Parr-Shaker. Upon complete consumption of the starting material, the vessel was flushed with $N_2$ to purge any remaining $H_2$. The reaction mixture was then filtered as a warm solution through a plug of celite to remove the catalyst. The filtrate was then reduced under vacuum to yield 12.9 g (99%) of the expected product.

Example 4

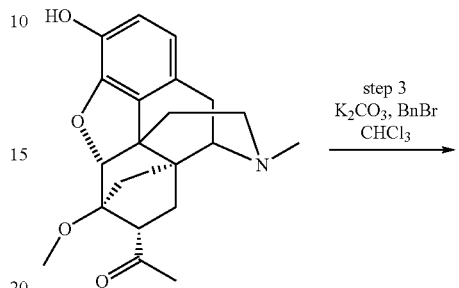

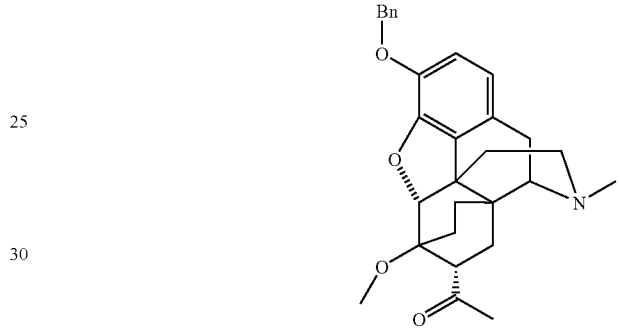

The reduced Diels-Alder adduct (24.0 g, 65 mmol) formed according to Example 4 and ground $K_2CO_3$ (45.0 g, 326 mmol) were charged to a 500 mL three neck round bottom flask that was equipped with a mechanical stirring device and a reflux condenser. 200 mL of $CHCl_3$ and then benzyl bromide (9.3 mL, 13.4 g, 78.3 mmol) was added to the flask. The reaction mixture was then heated to reflux for six hours. After allowing the reaction mixture to cool to room temperature, it was filtered to remove the $K_2CO_3$, washing the solids with excess $CHCl_3$. The filtrate was then reduced in vacuo and azeo dried (3×100 mL) with toluene. This crude material was then directly used for the Grignard reaction.

Example 5

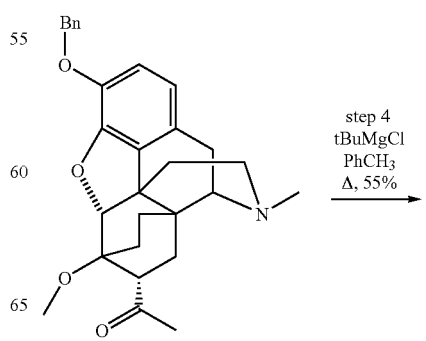

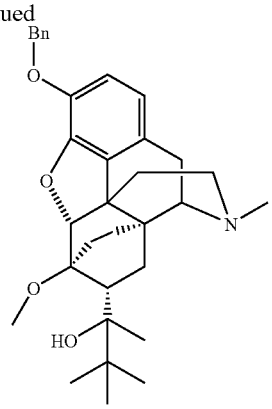

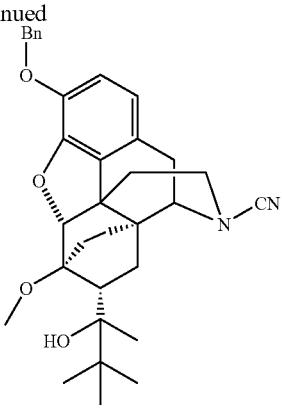

Prior to use, all glassware was oven dried overnight at 150° C. A 1-liter 4-neck round bottom flask was fitted with a mechanical stirrer, a graduated addition funnel, a distillation head and a thermocouple. The apparatus was assembled while it was still hot and was allowed to cool to room temperature under a nitrogen atmosphere. 1M t-BuMgCl 222 ml (222 mmol) was added to the flask followed by 250 ml of anhydrous toluene. The solution was distilled until a pot temperature of 100° C. was achieved. To the hot solution was added 20.4 g (44.4 mmol) of benzylated ketone formed according to example 5 in 50 ml of anhydrous toluene over 15 minutes. The reaction was heated at 100 to 105° C. for 4 hours then allowed to cool to room temperature. The reaction mixture was cooled below 10° C. using an ice bath and quenched with 153 ml of 4N $NH_4Cl$ while keeping the internal temperature below 30° C. Concentrated HCl (22 ml) was added to the heterogeneous mixture, thereby lowering the pH to 4. The organic and aqueous layers were separated, and the aqueous layer and the reaction vessel were extracted two times with 200 ml portions of $CHCl_3$. The combined organic layers were washed with 200 ml of water and concentrated in vacuo to afford an oily residue. After the reaction work-up, the crude oil was dissolved in approximately 200 mL of ethyl acetate and charged with approximately 30 grams of silica gel. The resulting mixture was then reduced in vacuo to produce the product solid bound to silica gel. This material was then purified by silica gel flash column chromatography using 2:1 Heptanes:Ethyl Acetate with 1% triethyl amine. Fractionation of the eluent yields 13.6 grams of 93% pure product.

Example 6

The tertiary alcohol starting material (18.2 g, 35.2 mmol) formed according to Example 6 was charged to a 500 mL round bottom flask equipped with a magnetic stir bar. The starting material was then dissolved in 100 mL of $CHCl_3$. After flushing the flask with $N_2$, the $K_2CO_3$ (1.7 g, 12.3 mmol) and the cyanogen bromide (5.6 g, 52.9 mmol) were added. The reaction mixture was brought to reflux, where it remains for 17 hours. After cooling to room temperature, the mixture was filtered to remove the $K_2CO_3$. The filtrate was then vigorously stirred with 90 mL of 2:1 $H_2O$:concentrated $NH_4OH$ for 45 minutes. The layers were then separated, washing the aqueous layer with an additional 50 mL of $CHCl_3$. The combined organic layers were dried with anhydrous $MgSO_4$, and reduced in vacuo. This yields a foamy solid after further drying under high vacuum. The foamy solid was then dissolved in 25 mL of toluene and 70 mL of heptane. The reaction mixture was placed in a water bath and brought to about 90° C. After an additional volume of 60 mL of heptane was added, the solution was slowly cooled with a precipitate forming at about 82° C. This reaction mixture was slowly cooled until room temperature when the bath was drop to 10° C. via an ice bath. After 30 minutes, the solids were isolated by vacuum filtration and washed with 40 mL of 3:1 heptane:toluene. This yielded 12.4 g (67%) of 93% clean material after drying.

Example 7

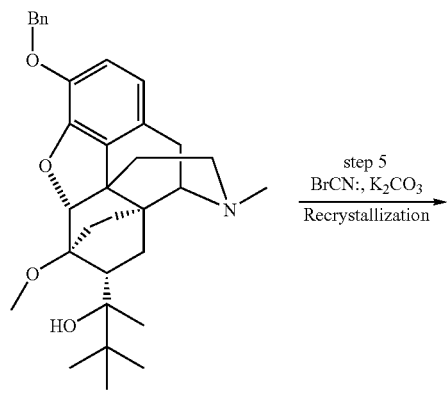

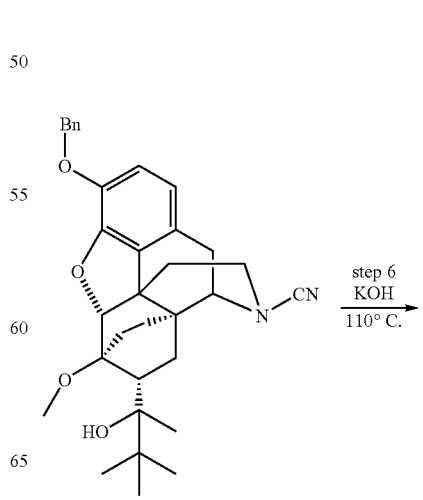

-continued

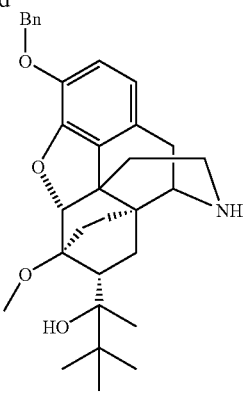

A 250 ml round bottom flask was charged with 20.2 g (360 mmol) of potassium hydroxide and 55 ml of diethylene glycol. The reaction mixture was heated to 110° C., and to the heated solution was added 9.5 g (18 mmol) of the N—CN compound formed according to Example 6. After heating for 27 hours, the reaction was cooled to room temperature and 150 ml of distilled water was added. The solid was collected after 15 minutes of mixing, and was washed with 100 ml of distilled water. After drying, 8.9 g of the product was obtained corresponding to a crude yield of 100%.

Example 8

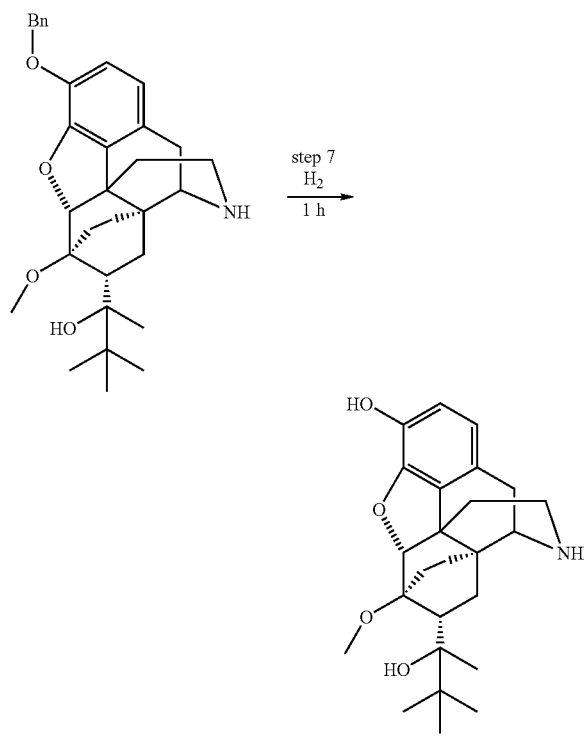

The secondary amine starting material (4.0 g, 8 mmol) formed according to Example 7 and 10% Pd/Carbon (0.4 g, 5% w/w by dry basis) were charged to a Parr-Shaker reaction bottle. The reactants were suspended in 30 mL of methanol, and attached to the Parr-Shaker apparatus. The reaction mixture was then flushed with 40 psi of $N_2$ eight times, and the reaction bottle was filled with $H_2$ to 40 psi. The reaction bottle was allowed to shake for 2.5 hours at 60° C., at which time LC analysis showed no remaining starting material. The reaction material was then filtered through a plug of celite to remove the catalyst. The filtrate was then reduced in vacuo to yield norbuprenorphine.

Example 9

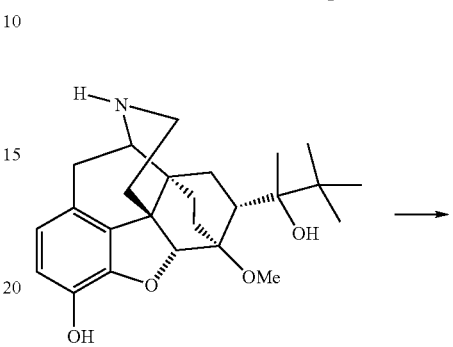

Formula VIII

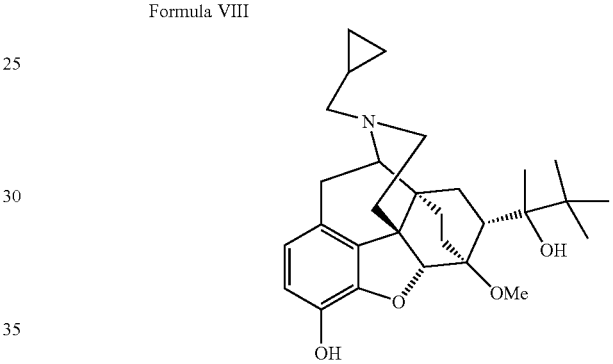

Formula IX

A mixture of 11.5 g of norbuprenorphine, 4.6 g of sodium bicarbonate, 4.85 g of cyclopropylmethyl bromide (1% butenyl bromide in it by GC) and 46 ml of dry DMF is heated in an oilbath at 80-100° C. for 4 hours until the reaction is substantially complete. The reaction mixture is transferred to a dropping funnel, with minimal DMF as a wash. The reaction mixture is added over 5 minutes to 160 ml of water, with mechanical stirring. (Adding water to the reaction yields a gum). The mixture is stirred for about 10 minutes and filtered. The filter cake is washed with 20 ml water. The HPLC will show about 90% by area of desired product, and 0.2-0.5% of an N-butenyl substituted impurity. The resulting product is dried, yielding about 12 g. The resulting product is boiled in 30 ml of methanol for about 30 minutes, cooled, and filtered to yield about 7.3 g buprenorphine.

There has been described a novel process for the production of norbuprenorphine and buprenorphine. While the process of this invention has been described with reference to specific reactions and examples, no intention is made by such reference to limit the scope of this invention unless expressly stated. Various modifications may be made in the materials and sequence of process steps as well as process combinations, which are adapted to suit the various process steps without departing from this invention. The foregoing description is given for clarity of understanding only and no unnecessary limitations should be understood there from, as modifications will be obvious to those skilled in the art.

The invention claimed is:

1. A method for producing norbuprenorphine, the method comprising:

a) reacting oripavine according to Formula I with methyl vinyl ketone to form a compound according to Formula II;

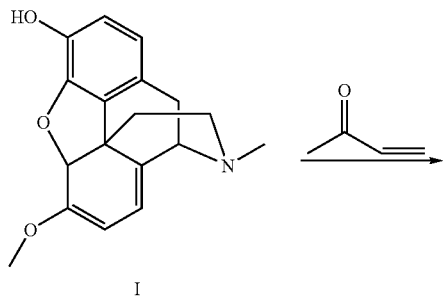

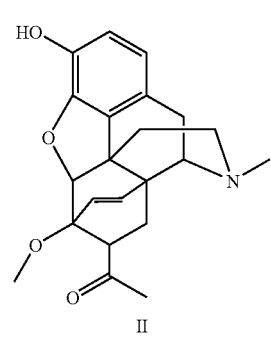

b) hydrogenating the compound according to Formula II to form a compound according to Formula III;

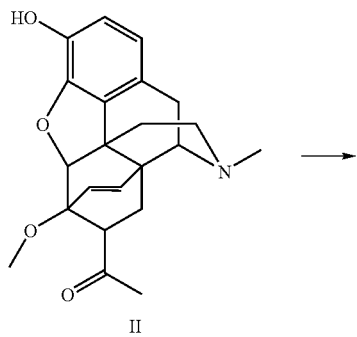

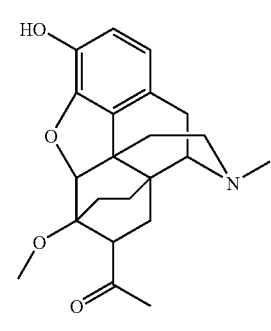

c) adding a t-butyl group to the compound according to Formula III to form a compound according to Formula X; and

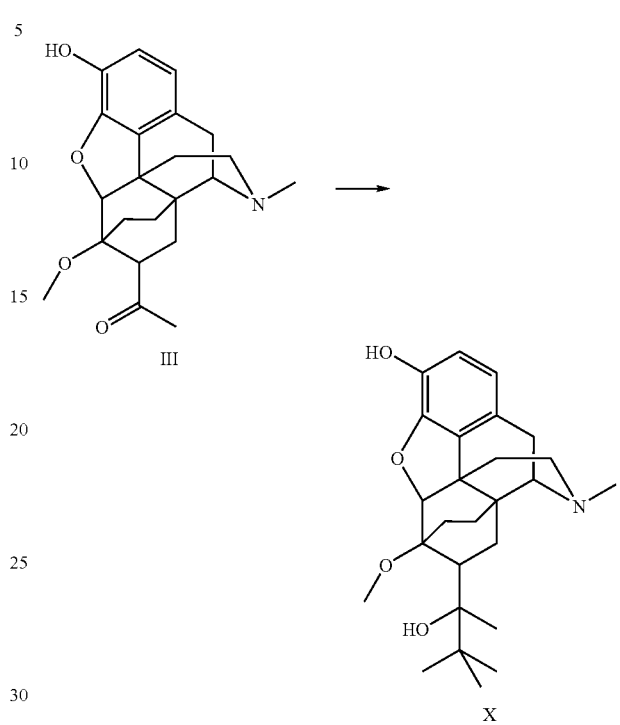

d) demethylating the nitrogen of the compound according to Formula X to form norbuprenorphine, Formula VIII

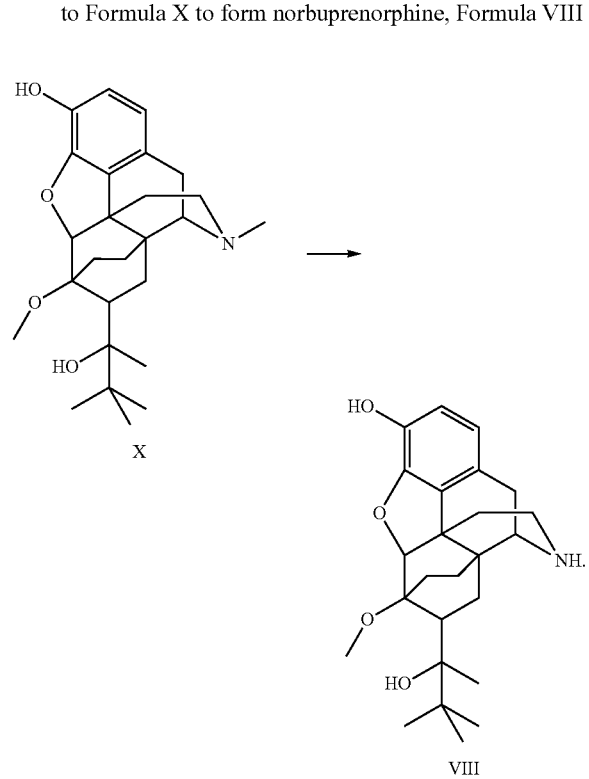

2. The method of claim 1 further including adding a cyclopropylmethyl group to the norbuprenorphine to form buprenorphine.

3. The method of claim 1 wherein a) and b) are combined in a single pot reaction sequence.

4. A method for producing norbuprenorphine, the method comprising:

a) reacting oripavine according to Formula I with methyl vinyl ketone to form a compound according to Formula II,

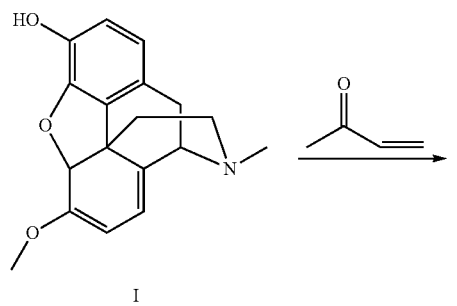

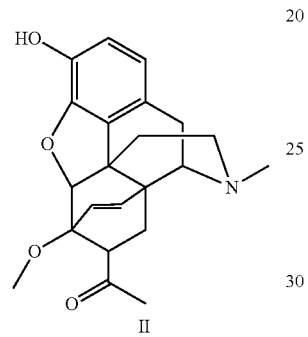

wherein the reaction has a yield of the compound of Formula II of at least 85%;

b) hydrogenating the compound according to Formula II to form a compound according to Formula III;

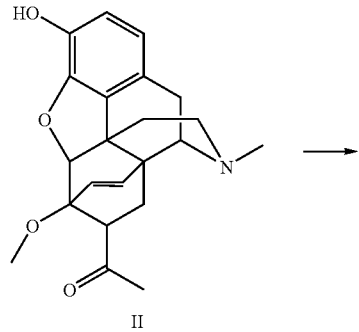

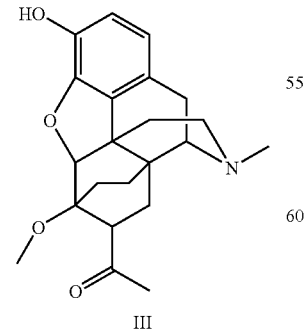

c) adding a t-butyl group to the compound according to Formula III to form a compound according to Formula X; and

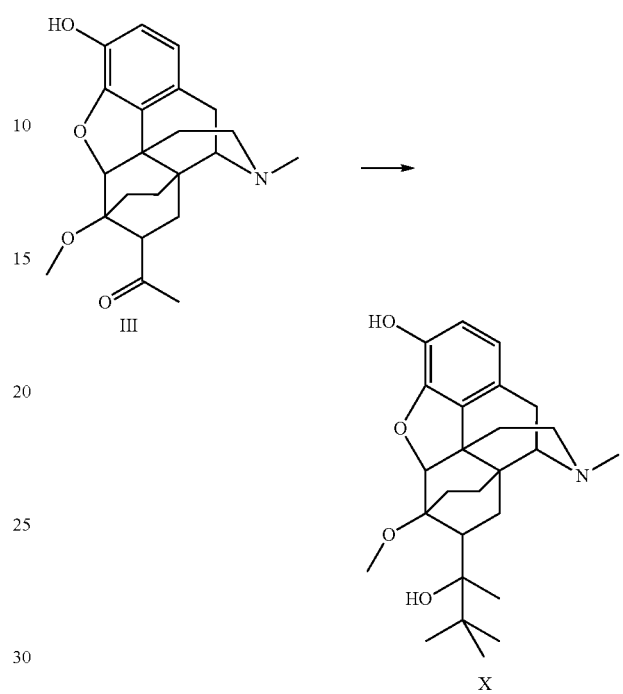

d) demethylating the nitrogen of the compound according to Formula X to form norbuprenorphine, Formula VIII.

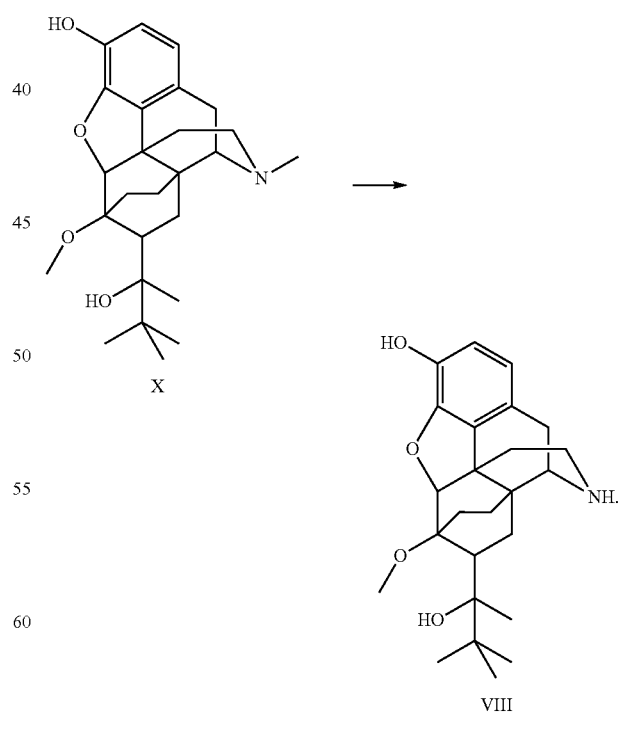

* * * * *